United States Patent
Kadokura et al.

(12) 
(10) Patent No.: US 6,469,189 B1
(45) Date of Patent: Oct. 22, 2002

(54) LIQUID DOUBLE ALKOXIDE OF NIOBIUM OR TANTALUM AND ALKALINE EARTH METAL, PRODUCTION METHOD THEREOF, AND PRODUCTION METHOD OF COMPLEX METAL OXIDE DIELECTRIC USING IT

(75) Inventors: Hidekimi Kadokura, Tokyo (JP); Yumie Okuhara, Sakado (JP)

(73) Assignee: Kabushikikaisha Kojundokagaku Kenkyusho, Saitama (JP)

( * ) Notice: Subject to any disclaimer, the term of this patent is extended or adjusted under 35 U.S.C. 154(b) by 0 days.

(21) Appl. No.: 09/506,140

(22) Filed: Feb. 17, 2000

(30) Foreign Application Priority Data

May 28, 1999 (JP) .......................................... 11-188065

(51) Int. Cl.$^7$ .......................... C07F 19/00; C07F 9/00; B05D 5/12; C04B 35/46; C23C 16/00
(52) U.S. Cl. .................. 556/28; 556/30; 556/42; 501/134; 501/135; 427/100; 427/126.3; 427/226; 427/255.21
(58) Field of Search .............................. 556/28, 42, 30; 501/134, 135; 427/100, 126.3, 226, 255.21

(56) References Cited

U.S. PATENT DOCUMENTS 5,654,456 A * 8/1997 Scott et al. .................... 556/28
5,683,614 A * 11/1997 Boyle .................... 252/62.9 R

* cited by examiner

Primary Examiner—Porfirio Nazario-Gonzalez
(74) Attorney, Agent, or Firm—Fattibene & Fattibene; Paul A. Fattibene; Arthur T. Fattibene (57) ABSTRACT

A novel compound shown by $M[N(OC_2H_5)_5(OC_2H_4OCH_3)]_2$, wherein M represents Sr or Ba, N represents Nb or Ta, which is a liquid at room temperature, is hard to be thermally dissociated, and has a vapor pressure of about 0.2 Torr at 190° C. The compound is produced by reacting 2 moles of $N(OC_2H_5)_5$ and from 1 to 1.1 moles of $M(OC_2H_4OCH_3)_2$ and then recovering the product by distillation. By using the compounds as raw materials for a CVD method, an $SrBi_2Ta_2O_9$ thin film or a $(Sr_{0.75}Ba_{0.25})Nb_2O_6$ thin film for semiconductor devices can be produced.

14 Claims, 4 Drawing Sheets

LIQUID DOUBLE ALKOXIDE OF NIOBIUM OR TANTALUM AND ALKALINE EARTH METAL, PRODUCTION METHOD THEREOF, AND PRODUCTION METHOD OF COMPLEX METAL OXIDE DIELECTRIC USING IT

FIELD OF THE INVENTION

The present invention relates to a novel liquid double alkoxide of niobium or tantalum and an alkaline earth metal, a production method thereof, and a production method of a complex metal oxide dielectric using thereof.

BACKGROUND OF THE INVENTION

Many dielectric thin films made of a complex metal oxide of niobium and/or tantalum and an alkaline earth metal show a high dielectric constant and a ferroelectricity. For example, $(Sr_pBa_q)Nb_2O_6$ (wherein, p+q=1) has been investigated and developed as an optical modulator and a infrared detector and $SrBi_2(Ta_xNb_y)_2O_9$ (wherein, x+y=1) has been investigated and developed as a nonvolatile memory, and they are partially used. As a method of producing these thin films using metal organic compounds as the raw materials, there are a sol-gel method, an MOD (Metalorganic deposition) method, and a CVD (Chemical vapor deposition) method. It is known that to make the film composition of an alkaline earth metal and niobium and/or tantalum a theoretical ratio and to crystallize at a lower temperature, it is effective to use a double alkoxide similar to the structure of an oxide crystal in an atomic order as the raw material.

As an example of the sol-gel method and the MOD method used in a solution state, Japanese Patent Laid-Open No. 80181/1999 (Production method of precursor for bismuth layer-structured perovskite ferroelectric thin film) discloses "a method of producing an Sr—Bi—Ta or —Nb-based composite alkoxide of Sr:Bi:Ta or Nb 1:2:2 (metal atomic ratio) having structure-controlled of an atomic arrangement, characterized in that an Sr—Bi double alkoxide $Sr[Bi(OR)_4]_2$ is formed by reacting an Sr alkoxide $(Sr(OR)_2)$ prepared from an Sr metal and a Bi alkoxide, $(Bi(OR)_3)$ in an alcohol, and then, the product is reacted with a Ta alkoxide $Ta(OR)_5$ or an Nb alkoxide $Nb(OR)_5$". In the invention, by analyzing the molecular structure by $^1$H-NMR, $^{13}$C-NMR, $^{93}$Nb-NMR, and FT-IR about the product obtained by drying the composite alkoxide solution using a rotary vacuum pump at a temperature of from 50 to 60° C., and it is concluded that the composite alkoxide is formed. Also, $Sr[Nb(OC_2H_5OCH_3)_6]_2$ is also disclosed in the above-described patent invention. However, these composite alkoxides are not recovered by distillation but are simple residues after distilling away the solvent. Therefore, all the molecules do not always completely form composite products, and also it is hard to say that the composition ratios are not autonomously determined to be the stoichiometric ratios. Also, it is not described in the specification of the invention whether or not the product can be recovered by distillation as the form of the composite alkoxide.

As examples of the CVD method using in a vapor-phase state, Japanese Patent Laid-Open No. 339716/1996 (Production method of bismuth layered ferroelectric thin film) discloses double isopropoxides such as $Sr[Ta(OCH(CH_3)_2)_6]_2$, etc., Japanese Patent Laid-Open No. 77592/1997 (Production method of bismuth layered ferroelectric thin film) discloses double ethoxides such as $Sr[Ta(OC_2H_5)_6]_2$, etc., and Japanese Patent Laid-Open No. 102254/1998 (Production method of tungsten bronze-type oxide dielectric thin film) discloses $Sr[Nb(OCH(CH_3)_2)_6]_2$, $Sr[Nb(OC_2H_5)_6]_2$, etc. All these double alkoxides are recovered by distillation or sublimation. However, these compounds are liquids at about 150° C. and solids at room temperature as shown in Table 1 below, which become defects in the production and the purification of the compounds and handling property as the raw material for CVD. In addition, it is reported by R. C. Mehrotra (Advances in Inorganic Chemistry and Radiochemistry, Vol. 26, 326(1983)) that these double isopropoxides are all solids and double ethoxides are viscous liquids excluding Ba-based ones, but the compounds synthesized and distilled by the present inventors are solids and the melting points are shown in Table 1 below.

TABLE 1

| Melting Points of Double Alkoxides | |
|---|---|
| $Sr[Nb (OC_2H_5)_6]_2$ | 115° C. |
| $Sr[Ta (OC_2H_5)_6]_2$ | 125° C. |
| $Ba[Nb (OC_2H_5)_6]_2$ | Solid at room temp. |
| $Ba[Ta (OC_2H_5)_6]_2$ | Solid at room temp. |

Furthermore, because at a temperature of at least about 180° C. having the vapor pressure of at least 0.1 Torr required for CVD, a thermal dissociation of a double alkoxide occurs little by little by the following formula II, the film composition is liable to be apart from the stoichiometric ratio.

$$Sr[Ta(OC_2H_5)_6]_2 \rightarrow [Sr(OC_2H_5)_2]_\infty + [Ta(OC_2H_5)_5]_2 \qquad II$$

Because $[Sr(OC_2H_5)_2]_\infty$ is a polymer and does not have volatility and $[Ta(OC_2H_5)_5]_2$ has a high vapor pressure, the $[Ta(OC_2H_5)_5]_2$ is intermixed with the vapor of $Sr[Ta(OC_2H_5)_6]_2$ and thus Ta/Sr of the vapor phase components becomes larger than 2. In order to remove this defect, the composition and the method disclosed in Japanese Patent Laid-Open No. 298760/1998 (Metal double alkoxide composition for vapor phase growth, supplying method thereof, and production method of complex metal oxide thin film using it) became necessary.

Furthermore, as a novel liquid compound for restraining the thermal dissociation of $Sr[Ta(OC_2H_5)_6]_2$, T. J. Leedham et al., 11th International Symposium on Integrated Ferroelectrics, Abstracts "Novel precursors for the MOCVD of ferroelectric thin films", 130C (1998. 3. 7) reported $Sr[Ta(OC_2H_5)_5(OC_2H_4N(CH_3)_2)]_2$. However, the detailed identification, production method, and properties thereof have not yet been described. That is, Sr—Nb-based, Ba—Nb-based, and Ba—Ta-based double alkoxides which are liquid compounds at room temperature and are hard to be thermally dissociated are not known.

SUMMARY OF THE INVENTION

The present invention provides a novel double alkoxide of niobium or tantalum and an alkaline earth metal, which is hard to be thermally dissociated, is a liquid at room temperature, and has a property capable of being distilled. Furthermore, the invention provides a production method of the compound and also provides a production method of a complex metal oxide dielectric using the above-described compound.

The present inventors have found that a novel double alkoxide represented by the following formula I is hard to be thermally dissociated, is a liquid at room temperature, and has the property capable of being distilled;

$$M[N(OC_2H_5)_5(OC_2H_4OR)]_2 \quad \quad I$$

wherein, M represents Sr or Ba, N represents Nb or Ta, and R represents an alkyl group having from 1 to 4 carbon atoms. In the formula I, the example of R is methyl, ethyl, propyl, isopropyl, or butyl but is preferably methyl.

The compound of this invention shown by the formula I can be easily produced by reacting $N(OC_2H_5)_5$ and $M(OC_2H_4OR)_2$. Also, the compound shown by the formula I wherein R is methyl can be easily produced by reacting $N(OC_2H_5)_5$ and $M(OC_2H_4OCH_3)_2$.

The compound of this invention shown by the formula I can be easily produced by reacting $N(OC_2H_5)_5$ and $M(OC_2H_4OR)_2$ and then recovering by distillation and the compound obtained has a correct stoichiometric ratio and a property of high purity.

Also, the compound of this invention shown by the formula I wherein R is methyl can be easily produced by reacting $N(OC_2H_5)_5$ and $M(OC_2H_4OCH_3)_2$ and recovering by distillation, and the compound obtained has a correct stoichiometric ratio and has a property of high purity.

Furthermore, in this invention, a complex metal oxide dielectric $MN_2O_6$ thin film can be easily produced using the compound of this invention shown by the formula I.

Also, in this invention, a complex metal oxide dielectric $MN_2O_6$ thin film can be easily produced using the compound of this invention shown by the formula I wherein R is methyl.

Moreover, in this invention, a complex metal oxide dielectric $MN_2O_6$ thin film can be easily produced by CVD using the compound of this invention shown by the formula I.

Also, in this invention, a complex metal oxide dielectric $MN_2O_6$ thin film can be easily produced by CVD using the compound of this invention shown by the formula I wherein R is methyl.

Furthermore, in this invention, a dielectric thin film shown by $(Sr_pBa_q)Nb_2O_6$ (wherein p+q=1) can be easily produced using the compounds shown by $Sr[Nb(OC_2H_5)_5(OC_2H_4OR)]_2$ and $Ba[Nb(OC_2H_5)_5(OC_2H_4OR)]_2$ (in both formulae, R represents an alkyl group having from 1 to 4 carbon atoms).

Also, in this invention, a dielectric thin film shown by $(Sr_pBa_q)Nb_2O_6$ (wherein p+q=1) can be easily produced using $Sr[Nb(OC_2H_5)_5(OC_2H_4OCH_3)]_2$ and $Ba[Nb(OC_2H_5)_5(OC_2H_4OCH_3)]_2$.

Still further, in this invention, a dielectric thin film shown by $(Sr_pBa_q)Nb_2O_6$ (wherein p+q=1) can be easily produced by CVD using the compounds shown by $Sr[Nb(OC_2H_5)_5(OC_2H_4OR)]_2$ and $Ba[Nb(OC_2H_5)_5(OC_2H_4OR)]_2$ (in both formulae, R represents an alkyl group having from 1 to 4 carbon atoms).

Furthermore, in this invention, a dielectric thin film shown by $(Sr_pBa_q)Nb_2O_6$ (wherein p+q=1) can be easily produced by CVD using $Sr[Nb(OC_2H_5)_5(OC_2H_4OCH_3)]_2$ and $Ba[Nb(OC_2H_5)_5(OC_2H_4OCH_3)]_2$.

Also, in this invention, a bismuth layered ferroelectric thin film shown by $SrBi_2(Ta_xNb_y)_2O_9$ (wherein x+y=1) can be easily produced using the compounds shown by $Sr[Ta(OC_2H_5)_5(OC_2H_4OR)]_2$ and $Sr[Nb(OC_2H5)_5(OC_2H_4OR)]_2$ (in both formulae, R represents an alkyl group having from 1 to 4 carbon atoms).

Furthermore, in this invention, a bismuth layered ferroelectric thin film shown by $SrBi_2(Ta_xNb_y)_2O_9$ (wherein x+y=1) can be easily produced using $Sr[Ta(OC_2H_5)_5(OC_2H_4OCH_3)]_2$ and $Sr[Nb(OC_2H_5)_5(OC_2H_4OCH_3)]_2$.

Also, in this invention, a bismuth layered ferroelectric thin film shown by $SrBi_2(Ta_xNb_y)_2O_9$ (wherein x+y=1) can be easily produced by CVD using the compounds shown by $Sr[Ta(OC_2H_5)_5(OC_2H_4OR)]_2$ and $Sr[Nb(OC_2H_5)_5(OC_2H_4OR)]_2$ (in both formulae, R represents an alkyl group having from 1 to 4 carbon atoms).

Furthermore, in this invention, a bismuth layered ferroelectric thin film shown by $SrBi_2(Ta_xNb_y)_2O_9$ (wherein x+y=1) can be easily produced by CVD using $Sr[Ta(OC_2H_5)_5(OC_2H_4OCH_3)]_2$ and $Sr[Nb(OC_2H_5)_5(OC_2H_4OCH_3)]_2$.

DESCRIPTION OF THE PREFERRED EMBODIMENTS

The novel compound of this invention is the compound represented by the following formula;

$$M[N(OC_2H_5)_5(OC_2H_4OR)]_2 \quad \quad I$$

wherein M represents Sr or Ba, N represents Nb or Ta, and R represents an alkyl group having from 1 to 4 carbon atoms.

Examples of the practical compound shown by the formula I are shown in Table 2 below.

TABLE 2

| Double Alkoxide of the Invention |
|---|
| Sr [Nb $(OC_2H_5)_5(OC_2H_4OCH_3)]_2$ |
| Sr [Ta $(OC_2H_5)_5(OC_2H_4OCH_3)]_2$ |
| Ba [Nb $(OC_2H_5)_5(OC_2H_4OCH_3)]_2$ |
| Ba [Ta $(OC_2H_5)_5(OC_2H_4OCH_3)]_2$ |
| Sr [Nb $(OC_2H_5)_5(OC_2H_4OC_2H_5)]_2$ |
| Sr [Ta $(OC_2H_5)_5(OC_2H_4OC_2H_5)]_2$ |
| Ba [Nb $(OC_2H_5)_5(OC_2H_4OC_2H_5)]_2$ |
| Ba [Ta $(OC_2H_5)_5(OC_2H_4OC_2H_5)]_2$ |
| Sr [Nb $(OC_2H_5)_5(OC_2H_4OC_3H_7)]_2$ |
| Sr [Ta $(OC_2H_5)_5(OC_2H_4OC_3H_7)]_2$ |
| Ba [Nb $(OC_2H_5)_5(OC_2H_4OC_3H_7)]_2$ |
| Ba [Ta $(OC_2H_5)_5(OC_2H_4OC_3H_7)]_2$ |
| Sr [Nb $(OC_2H_5)_5(OC_2H_4Oi—C_3H_7)]_2$ |
| Sr [Ta $(OC_2H_5)_5(OC_2H_4Oi—C_3H_7)]_2$ |
| Ba [Nb $(OC_2H_5)_5(OC_2H_4Oi—C_3H_7)]_2$ |
| Ba [Ta $(OC_2H_5)_5(OC_2H_4Oi—C_3H_7)]_2$ |
| Sr [Nb $(OC_2H_5)_5(OC_2H_4OC_4H_9)]_2$ |
| Sr [Ta $(OC_2H_5)_5(OC_2H_4OC_4H_9)]_2$ |
| Ba [Nb $(OC_2H_5)_5(OC_2H_4OC_4H_9)]_2$ |
| Ba [Ta $(OC_2H_5)_5(OC_2H_4OC_4H_9)]_2$ |

Furthermore, a mixture of the compounds shown in Table 2 above is also included in this invention.

Then, $Sr[Ta(OC_2H_5)_5(OC_2H_4OCH_3)]_2$ (strontium bis[tantalum (pentaethoxy)(2-methoxyethoxide)] is explained as an example of the compound of this invention.

According to the method of this invention, $Sr[Ta(OC_2H_5)_5(OC_2H_4OCH_3)]_2$ is obtained by reacting 2 moles of $Ta(OC_2H_5)_5$(tantalum ethoxide) and from 1 to 1.1 moles of $Sr(OC_2H_4OCH_3)_2$ (strontium(2-methoxyethoxide)) in a solvent such as toluene, etc., or solventless at a proper temperature of from 100 to 200° C. for from 1 to 12 hours. After distilling off the solvent from the reaction product liquid obtained, the residue is distilled under vacuum of about 0.3 Torr and the distillate obtained at a temperature of from 195 to 210° C. is the isolated desired compound.

The identification applied to the isolated compound in Example 1 and the properties of the compound are shown below.

(1) Composition analysis:

Result of ICP-AES analysis:

Sr 8.40% Ta 34.1%

(The formula weight of $Sr[Ta(OC_2H_5)_5(OC_2H_4OCH_3)]_2 = SrTa_2C_{26}H_{64}O_{14}$ 1050.3, the calculated values Sr 8.34%, Ta 34.5%).

From the analytical values, Ta/Sr became 1.97, which coincides with the stoichiometric ratio 2 within an analytical error.

The residual organic components became 57.5% on balance, which was near the calculated value 57.16%.

(2) Impurity analysis:

Result of ICP-AES analysis (unit ppm):

Mg 1, Ca 25, Ba 91, Fe 1

The result showed the compound was of high purity.

(3) Molecular weight:

The molecular weight was measured by a benzene cryoscopic method.

Sample 1.5753 g Benzene 20.0 g $\Delta T=0.358°$ C., 0.403° C., 0.391° C. Average 0.384° C.

Thus, the molecular weight=1050

Association degree 1.00

(4) $^1$H-NMR

Measurement conditions:

Apparatus: BRUKER AC-300P FT-NMR

Observed frequency: 300.13 MHz

Solvent: Benzene-$d_6$

Chemical shift standard: TMS

Concentration: about 8 mg/0.7 ml

Temperature: Room temperature

Figure 1:
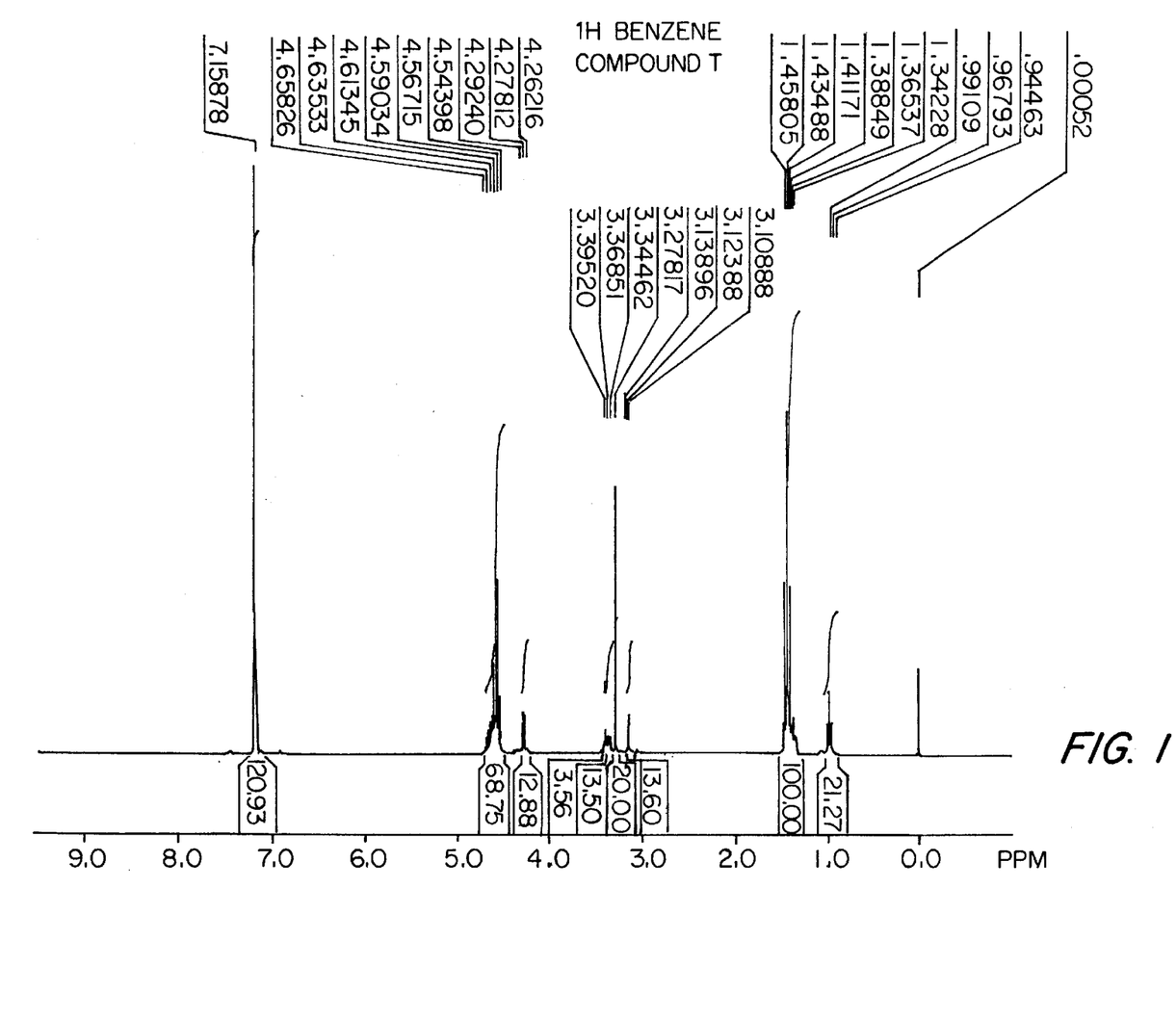
FIG. 1 is a graph showing the measurement result of $Sr[Ta(OC_2H_5)_5(OC_2H_4OCH_3)]_2$ by $^1$H-NMR.

The measurement results are shown in FIG. 1.

The spectrum and the assignment are as shown in Table 3 below.

TABLE 3

| $\delta_H$(ppm) | Pattern | J | Proton No. | Assignment |
|---|---|---|---|---|
| 0.968 | t | 6.98 | 6H | ? |
| 1.412 | t | 6.96 | 30H | —OCH$_2$C$\underline{H}_3$ |
| 3.124 | t | 4.50 | 4H | ? |
| 3.278 | s |  | 6H | —OCH$_2$CH$_2$OC$\underline{H}_3$ |
| 3.369 | t |  | 4H | —OCH$_2$C$\underline{H}_2$OCH$_3$ |
| 4.278 | t | 4.50 | 4H | —OC$\underline{H}_2$CH$_2$OCH$_3$ |
| 4.590 | q(m) | 6.93 | 20H | —OC$\underline{H}_2$CH$_3$ |

There are obscure peaks at $\delta_H$=0.968 and =3.124 but others can be assigned to $Sr[Ta(OC_2H_5)_5(OC_2H_4OCH_3)]_2$. One of the reasons of causing these obscure peaks is considered to be that a hydrolysis may occur during the preparation of a sample tube for NMR.

(5) FT-IR

Measurement condition:

Apparatus: SIMADZU FT-IR 8600

Measuring method: Liquid film method

Figure 2:
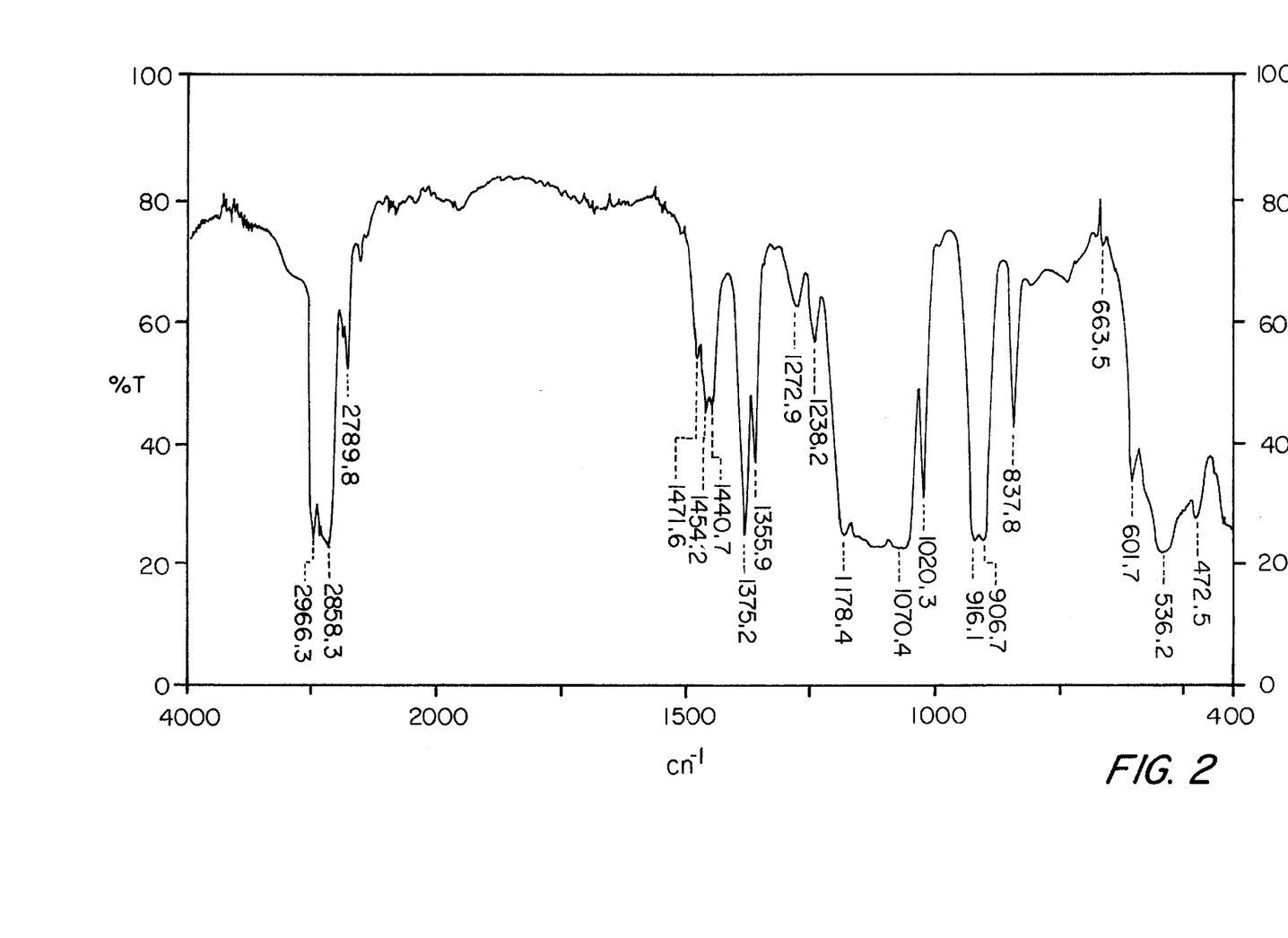
FIG. 2 is a graph showing the measurement result of $Sr[Ta(OC_2H_5)_5(OC_2H_4OCH_3)]_2$ by FT-IR.

The measurement result is shown in FIG. 2

Spectra (cm$^{-1}$):

2966, 2858, 2710, 1472, 1454, 1441, 1375, 1356, 1273, 1238, 1178, 1070, 1020, 916, 901, 837, 664, 602, 536, 473.

The low frequencies 664, 602, 536, and 473 are vibrations of Ta-O and Sr-O.

(6) Vapor pressure:

Measured value by a gas saturation method:

0.23 Torr/190° C.

(7) Property and melting point:

The compound was a colorless transparent liquid at room temperature and the melting point thereof was below 0° C.

(8) Liquid density:

1.46 g/cm$^3$/20° C.

(9) Kinematic viscosity:

About 20 cSt/20° C.

(10) TG-DTA:

Measurement condition:

Sample weight: 27.7 mg

Atmosphere: Ar 1 atm.

Temperature raising rate: 10.0° C./minute

Figure 3:
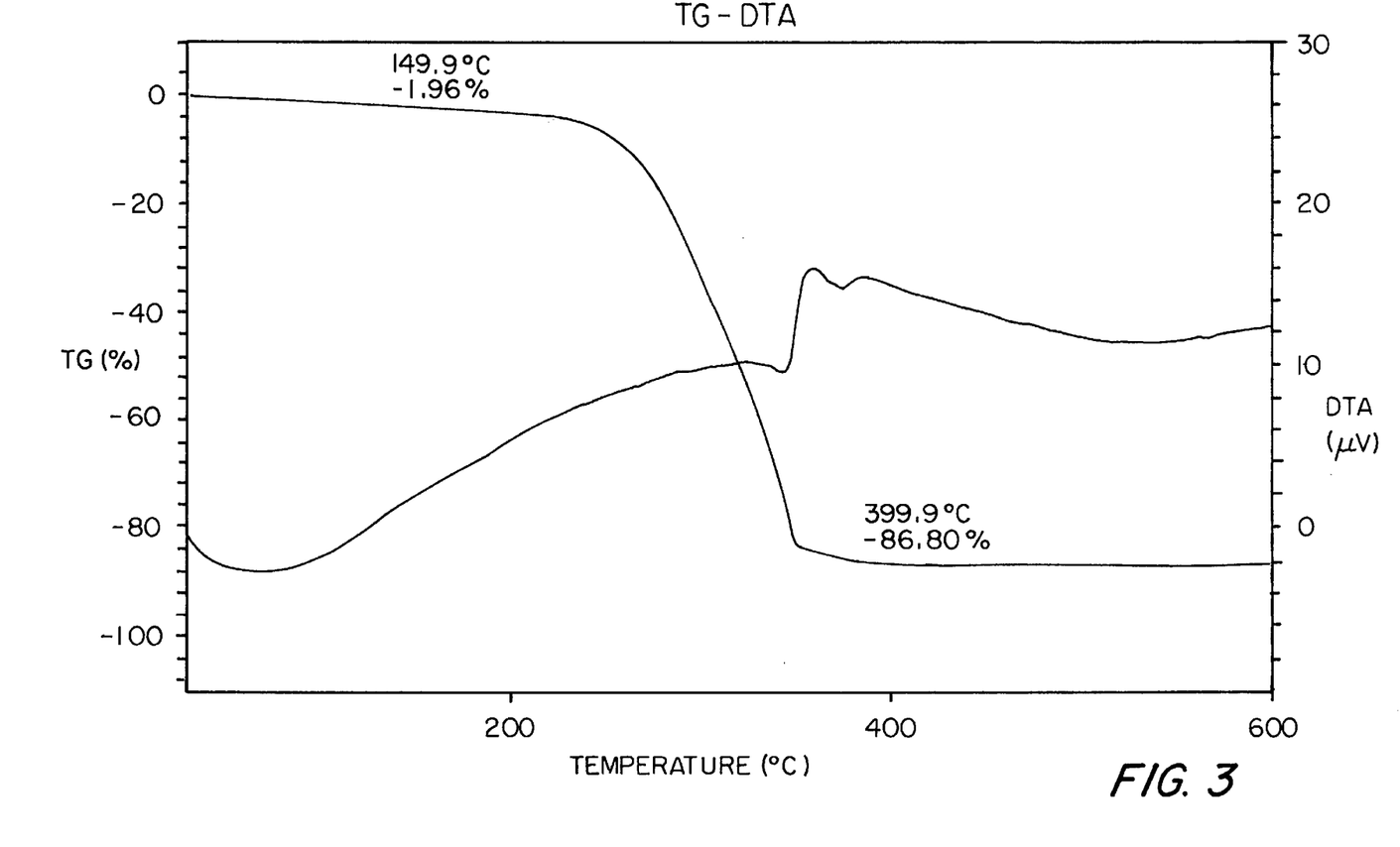
FIG. 3 is a graph showing the measurement result of $Sr[Ta(OC_2H_5)_5(OC_2H_4OCH_3)]_2$ by TG-DTA.

The measurement result is shown in FIG. 3. The reason that a reduced amount of about 2% until the temperature became 150° C. is presumed to be that the compound reacts with moisture in air during setting the sample to the measurement system and an alcohol formed by the hydrolysis was volatiled.

(11) Solubility:

The solubility (g/100 ml-toluene, 20° C.) in toluene was at least 3700 g.

The solubility (g/100 ml-THF, 20° C.) in THF was at least 3700 g.

(12) Heat stability:

By analyzing the composition of the evaporated material, whether or not a thermal dissociation occurred was determined.

Measurement method:

A Pyrex glass-made container for evaporation (diameter 30 mm, height 150 mm, volume 100 ml, and containing 40 ml of zirconia balls of 4 mm diameter to get good gas-liquid contact) having bubbling inlet of a carrier gas at a bottom portion and an outlet of the gas at the upper vapor-phase portion can be maintained at a constant pressure by an evacuating apparatus having a condenser connected to the oultlet of the container. In the evaporation container was placed 29 g of the compound, $Sr[Ta(OC_2H_5)_5(OC_2H_4OCH_3)]_2$ isolated in Example 1, and the compound was maintained at 190° C. While maintaining the whole system at 10 Torr, 30 sccm of Ar carrier gas was bubbled into the container from the inlet, and the gas saturated with the vapor of the double alkoxide was took out from the outlet, and condensed at the condenser. The gas feed was stopped every 60 minutes, the condensate was dissolved in toluene and recovered, and the determinations of Sr and Ta thereof were carried out by an ICP-AES analysis.

The atomic ratio of Ta/Sr is shown in Table 4.

TABLE 4

Amount and atomic ratio of evaporation recovered material

| Condensate | Weight (g) | Ta/Sr Atomic ratio |
|---|---|---|
| 1st Recovered material | 2.00 | 1.91 |
| 2nd Recovered material | 1.89 | 1.96 |
| 3rd Recovered material | 1.96 | 1.97 |
| 4th Recovered material | 2.01 | 1.96 |
| 5th Recovered material | 1.96 | 1.97 |

TABLE 4-continued

Amount and atomic ratio of evaporation recovered material

| Condensate | Weight (g) | Ta/Sr Atomic ratio |
|---|---|---|
| 6th Recovered material | 1.96 | 1.96 |
| 7th Recovered material | 1.47 | 1.92 |
| 8th Recovered material | 1.29 | 1.93 |
| 9th Recovered material | 1.45 | 1.90 |
| Sum total of accumulated recovered materials | 15.99 | |

From the results, it has been confirmed that because from the first, the compound was evaporated as the double alkoxide of Ta/Sr=2 and excessive Ta(OEt)$_5$ was not contained therein, the compound was not thermally dissociated.

Also, the amount of content left in the evaporation container after the test was 13 g, and as the result of the composition analysis thereof, Sr was 8.64%, Ta was 33.4%, and Ta/Sr.was 1.87. It can be said that the composition was considerably similar to the charged composition.

The measurement results of Sr[Ta(OC$_2$H$_5$)$_6$]$_2$ at 190° C. made by almost the same method as above are shown in Table 3 of Japanese Patent Laid-Open No. 298760/1998. In the published invention, the Ta/Sr ratio of the 1st recovered material was as high as 4.60 and the ratio became lower as the measurement of the recovered material progressed, but the ratio of even the 9th recovered material was still as high as 2.59. Because the vapor pressure of Sr[Ta(OC$_2$H$_5$)$_6$]$_2$ at 190° C. is 0.25 Torr, which is almost the same as 0.23 Torr of the compound of the present invention, it can be said that the compound of the present invention forms a stable double alkoxide which is hard to be thermally dissociated and has a good composition stability as a CVD raw material.

Figure 4:
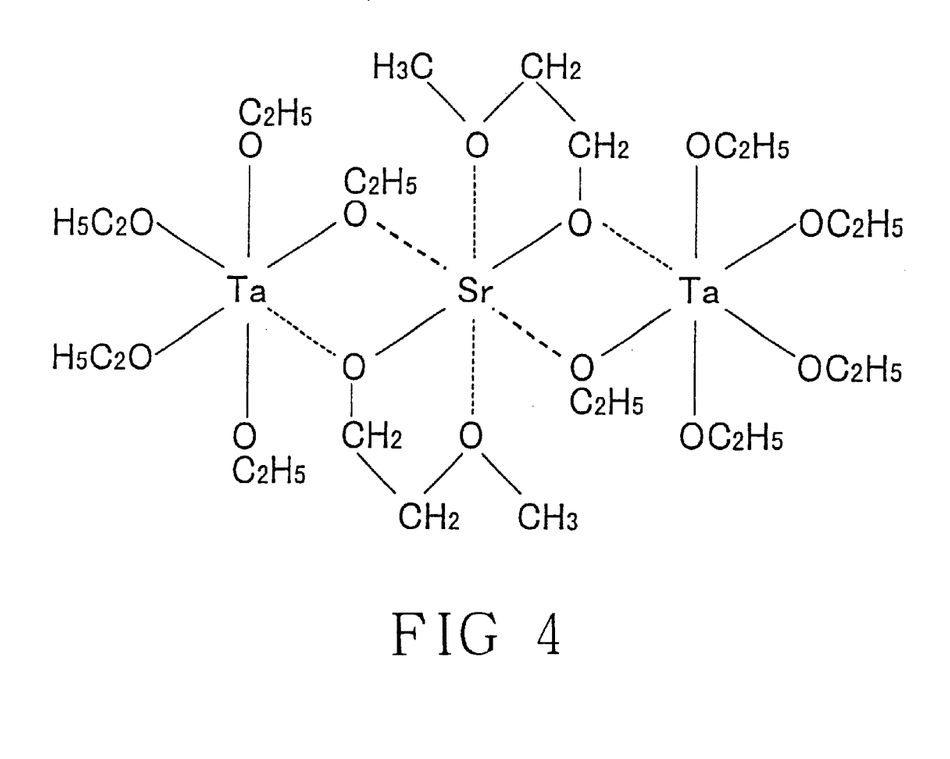
FIG. 4 is a supposed view of the molecular structure of $Sr[Ta(OC_2H_5)_5(OC_2H_4OCH_3)]_2$.

By synthetically deciding mainly from the composition analysis, the molecular weight, $^1$H-NMR, and FT-IR of the results described above, the compound is identified to be Sr[Ta(OC$_2$H$_5$)$_5$(OC$_2$H$_4$OCH$_3$)]$_2$. The possible molecular structure is shown in FIG. 4.

The present invention also relates to a method of producing the compound of this invention excellent in the mass production.

According to the method of this invention, M[N(OC$_2$H$_5$)$_5$(OC$_2$H$_4$OR)]$_2$ (wherein, M represents Sr or Ba, N represents Nb or Ta, and R represents an alkyl group having from 1 to 4 carbon atoms) is obtained by reacting 2 moles of N(OC$_2$H$_5$)$_5$ and from 1 to 1.1 moles of M(OC$_2$H$_4$OR)$_2$ in a solvent such as toluene, etc., or solventless at a proper temperature of from 100 to 200° C. for from 1 to 12 hours. In this case, by substantially adjusting the charging mole ratio to the stoichiometric ratio, the product can be used without recovering by distillation.

It is preferred that after distilling off the solvent from the reaction product, the residue is distilled under vacuum of about 0.3 Torr and the fraction obtained at a temperature of from about 190 to 240° C. is obtained. The fraction is the pure product of the desired compound and it is possible to make the autonomously determined stoichiometric ratio N/M=2. In this case, when the charging ratio is slightly excessive side of M(OC$_2$H$_4$OR)$_2$ from the stoichiometric ratio, unreacted N(OC$_2$H$_5$)$_5$ is not left and the recovery of the desired compound by distillation becomes easy. By distilling, N(OC$_2$H$_5$)$_5$, which is the raw material having high volatility and has the possibility of being slightly left unreacted, can be removed, and also alkoxides of impure elements having higher boiling point and nonvolatile polymers and oxides formed by decomposition and condensation can be conveniently removed.

Now, M(OC$_2$H$_4$OR)$_2$ used in this method can be easily produced by reacting a metal, M (Sr or Ba) and ROCH$_2$CH$_2$OH (2-alkoxyethanol) at a temperature of from about room temperature to 50° C. for from 1 minute to 1 hour and distilling off under reduced pressure the excessive raw material alcohol at about 100° C.

Examples of the 2-alkoxyethanol used in the above reaction include 2-methoxyethanol (classical name: methyl cellosolve), 2-ethoxyethanol (classical name: ethyl cellosolve), 2-propoxyethanol, 2-isopropoxyethanol, and 2-butoxyethanol.

Also, the present invention relates to a method of producing a complex metal oxide dielectric containing MN$_2$O$_6$ as the constitutional component using the compound of this invention. Examples of these dielectrics include (Sr$_p$Ba$_q$)Nb$_2$O$_6$ (wherein, p+q=1), SrBi$_2$(Ta$_x$Nb$_y$)$_2$O$_9$ (wherein, x+y=1), etc.

By decomposing or oxidizing the compound of this invention as the raw material in an oxidative atmosphere at a temperature of from 300 to 800° C., an oxide having the theoretical ratio N/M=2 can be easily produced. It is considered that the molecular structure of the compound of this invention is similar to a complex metal oxide and the crystallization of the complex metal oxide is liable to occur at a lower temperature.

For producing the oxide thin film, a sol-gel method, an MOD method, or a CVD method is used using the compound of this invention. Preferably, by using the compound of this invention obtained by distillation-recovering, a complex metal oxide dielectric having less impurities can be obtained at a stoichiometric ratio.

Also, because the compound of this invention becomes a vapor, the compound is suitable for producing an oxide thin film using the raw material for a CVD method.

In the case of using for the CVD method, examples of the supplying method of the compound of this invention include the following two:

(1) the compound of this invention is maintained at a temperature of from 150 to 250° C., and the vapor thereof is supplied by bubbling of a carrier gas, (2) the compound of this invention is dissolved in an organic solvent such as THF, hexane, octane, butyl acetate, etc., to form a solution thereof and the solution is passed through a liquid mass flow controller and evaporated by a evaporator.

The compound of this invention has a high solubility in an organic solvent and a solution thereof is easily prepared.

In the case of producing the thin film of (Sr$_p$Ba$_q$)Nb$_2$O$_6$ (wherein p+q=1), for example, Sr[Nb(OC$_2$H$_5$)$_5$(OC$_2$H$_4$OCH$_3$)]$_2$ and Ba[Nb(OC$_2$H$_5$)$_5$(OC$_2$H$_4$OCH$_3$)]$_2$ may be used as a pre-mixed solution. Because the vapor pressures of these compounds are almost the same, the mixing ratio of them may be p:q but when the film composition differs a little from the aimed one, the mixing ratio may be corrected a little. As a matter of course, after evaporating each compound separately, the vapors formed may be mixed.

The compound of this invention is hard to be thermally dissociated but in a CVD method, when the conditions and apparatus capable of preventing the thermal dissociation of the compound as completely as possible are employed until the vapor of the compound reaches a heated substrate, the film composition formed on the substrate can be made the stoichiometric ratio.

In the case of $SrBi_2(Ta_xNb_y)_2O_9$ (wherein, x+y=1), the same can be applied to $Sr[Nb(OC_2H_5)_5(OC_2H_4OCH_3)]_2$ and $Sr[Ta(OC_2H_5)_5(OC_2H_4OCH_3)]_2$, which are the combination of the raw materials.

In the case of producing the thin film of $SrBi_2(Ta_xNb_y)_2O_9$ (wherein, x+y=1) by the CVD method, as the bismuth compound of the raw material, triphenylbismuth, tri(orthotolyl)bismuth, bismuth tertiary-butoxide, bismuth tertiary-amyloxide, stabilized trimethylbismuth, tris(dipivaloylmethanato)bismuth, etc., can be used.

As the CVD method, ECR-plasma CVD method, laser CVD method, etc., can also be used other than thermal CVD method. As the oxidative gas, there are $O_2$, $N_2O$, etc.

EXAMPLE 1

Production of $Sr[Ta(OC_2H_5)_5(OC_2H_4OCH_3)]_2$ (strontium bis[tantalum(pentaethoxy)(2-methoxyethoxide)]:

A 500 ml four-neck flask equipped with a reflux condenser, a thermometer, and a stirrer was vacuumed and replaced with argon atmosphere, 70 ml (0.89 mole) of 2-methoxyethanol dehydrated with molecular sieve 3A was charged in the flask and then 8.8 g (0.100 mole) of strontium pieces were charged therein. Then, when the mixture was heated to 40° C. with stirring, they reacted within 1 to 2 minutes, and the metal pieces were vanished. After the unreacted raw material, 2-methoxyethanol was distilled off under a reduced pressure at 100° C., translucent white solids were formed, which were $Sr(OC_2H_4OCH_3)_2$ (strontium(2-methoxyethoxide)). Then, 250 ml of toluene was charged in the flask followed by heating to 100° C. to dissolve $Sr(OC_2H_4OCH_3)_2$. Then, 76.6 g (0.189 mole) of $Ta(OC_2H_5)_5$ (tantalum ethoxide) was charged therein and the mixture was refluxed for 8 hours. The liquid formed was colorless and transparent. Then, under a reduced pressure, toluene was distilled off at 100° C. Then, the condenser was removed and a distillation was carried out under vacuum of 0.3 Torr. In this case, no distillate was formed until 180° C., which showed that there was neither unreacted tantalum ethoxide nor dissociated tantalum ethoxide. When the temperature was further raised, the distillation occurred and the product was almost distilled at a distillation temperature of from 195 to 210° C. to obtain 96 g of a colorless, transparent oily liquid. As the result of identifying the liquid, the product was $Sr[Ta(OC_2H_5)_5(OC_2H_4OCH_3)]_2$ (strontium bis[tantalum(pentaethoxy)(2-methoxyethoxide)] (0.091 mole). The yield was 96% based on the tantalum ethoxide used.

EXAMPLE 2

Production of $Sr[Nb(OC_2H_5)_5(OC_2H_4OCH_3)]_2$ (strontium bis[niobium(pentaethoxy)(2-methoxyethoxide)]:

A 300 ml four-neck flask equipped with a reflux condenser, a thermometer, and a stirrer was vacuumed and replaced with an argon atmosphere, 30 ml (0.37 mole) of 2-methoxyethanol dehydrated with molecular sieve 3A was charged in the flask and then 3.8 g (0.043 mole) of strontium pieces were charged therein. Then, when the mixture was heated to 40° C. with stirring, they reacted within 1 to 2 minutes, and the metal pieces were vanished. After the unreacted raw material, 2-methoxyethanol was distilled off under a reduced pressure at 100° C., translucent white solids were formed, which were $Sr(OC_2H_4OCH_3)_2$ (strontium(2-methoxyethoxide)). Then, 100 ml of toluene was charged and the mixture was heated to 100° C. to dissolve $Sr(OC_2H_4OCH_3)_2$. Then, 25.4 g (0.080 mole) of $Nb(OC_2H_5)_5$ (niobium ethoxide) was charged therein and the mixture was refluxed for 5 hours. The liquid formed was light-brown and transparent. Then, under a reduced pressure, toluene was distilled off at 100° C. Then, the condenser was removed and a distillation was carried out under vacuum of 0.3 Torr. In this case, no distillate was formed until 180° C., which showed that there was neither unreacted niobium ethoxide nor niobium ethoxide formed by dissociation. When the temperature was further raised, the distillation occurred and the product was almost distilled at a distillation temperature of from 195 to 205° C. to obtain 33 g of a light-yellow, transparent oily liquid.

The density of the liquid at room temperature was 1.22 g/cm³ and the melting point thereof was below 0° C. As the results of the composition analysis, Sr was 9.67%, Nb was 20.9%, and Nb/Sr was 2.05.

In the theoretical values of $Sr[Nb(OC_2H_5)_5(OC_2H_4OCH_3)]_2$ (strontium bis[niobium(pentaethoxy)(2-methoxyethoxide)], Sr is 10.0% and Nb is 21.3%, and thus the analytical values coincided with the theoretical values within an erroneous range. Thus, it was decided that the liquid was desired $Sr[Nb(OC_2H_5)_5(OC_2H_4OCH_3)]_2$. The amount of the product was 0.0377 mole and the yield thereof was 94% based on the niobium ethoxide used.

As the results of analyzing impurities (unit: ppm), Mg was 1, Ca was 39, Ba was 130, Fe was 1, and Na was 1, which showed that the product was of high purity.

EXAMPLE 3

Production of $Ba[Nb(OC_2H_5)_5(OC_2H_4OCH_3)]_2$ (barium bis[niobium(pentaethoxy)(2-methoxyethoxide)]:

A 300 ml four-neck flask equipped with a reflux condenser, a thermometer, and a stirrer was vacuumed and replaced with an argon atmosphere, 30 ml (0.37 mole) of 2-methoxyethanol dehydrated with molecular sieve 3A was charged in the flask and then 6.1 g (0.044 mole) of barium pieces were charged therein. The mixture reacted within 1 to 2 minutes at room temperature, and the metal pieces were vanished. After the unreacted raw material, 2-methoxyethanol was distilled off under a reduced pressure at 100° C., white solids were formed, which were $Ba(OC_2H_4OCH_3)_2$ (barium(2-methoxyethoxide)). Then, 100 ml of toluene was charged in the flask and the mixture was heated to 100° C. to dissolve $Ba(OC_2H_4OCH_3)_2$. Then, 25.1 g (0.079 mole) of $Nb(OC_2H_5)_5$ (niobium ethoxide) was charged therein and the mixture was refluxed for 5 hours. The liquid formed was light-brown transparent. Then, under a reduced pressure, toluene was distilled off at 100° C. Then, the condenser was removed and a distillation was carried out under vacuum of 0.3 Torr. In this case, no distillate was formed until 180° C., which showed that there was neither unreacted niobium ethoxide nor niobium ethoxide formed by dissociation. When the temperature was further raised, the distillation occurred and the product was almost distilled at a distillation temperature of from 200 to 215° C. to obtain 34 g Qf a light-yellow, transparent oily liquid.

The density of the liquid at room temperature was 1.26 g/cm³ and the melting point thereof was below OC. As the results of the composition analysis, Ba was 14.6%, Nb was 20.5%, and Nb/Sr was 2.05.

In the theoretical values of $Ba[Nb(OC_2H_5)_5(OC_2H_4OCH_3)]_2$ (barium bis[niobium(pentaethoxy)(2-methoxyethoxide)], Ba is 14.9% and Nb is 20.1%, and thus the analytical values coincided with the theoretical values within an erroneous range. Thus, it was decided that the liquid was desired $Ba[Nb(OC_2H_5)_5(OC_2H_4OCH_3)]_2$. The amount of the product was 0.0368 mole and the yield thereof was 93% based on the niobium ethoxide used.

As the results of analyzing impurities (unit: ppm), Mg was 1, Ca was 67, Sr was 730, and Fe was 3, which showed that the product was of high purity.

EXAMPLE 4

Production of $SrBi_2Ta_2O_9$ thin film of bismuth layer-structured perovskite by CVD method:

A raw material container of a vacuum heat CVD apparatus system (total pressure 10 Torr) was filled with 35 g of $Sr[Ta(OC_2H_5)_5(OC_2H_4OCH_3)]_2$ obtained in Example 1, and the container was maintained at a constant temperature of 180° C., then 30 sccm of argon was introduced by bubbling and sent to a thermal decomposition chamber together with the vapor of $Sr[Ta(OC_2H_5)_5(OC_2H_4OCH_3)]_2$ evaporated. At the same time, 35 g of $Bi[OC(CH_3)_2C_2H_5]_3$ (bismuth tertiary-amyloxide) was filled in another raw material container, the container was maintained at a constant temperature of 100° C., 50 sccm of an argon gas was introduced and sent to the thermal decomposition chamber together with the vapor of the compound evaporated. These two kinds of gases were mixed with 30 sccm of an oxygen gas at the inlet of the thermal decomposition chamber.

In the thermal decomposition chamber, a $Pt/SiO_2/Si$ substrate was heated to 400° C., the mixed gas containing the vapors was introduced onto the substrate to cause a thermal decomposition accumulation. Then, the amount of an oxygen gas introduced was increased, the temperature was raised, and a crystallization treatment was applied at 750° C. for 30 minutes. Thus, a thin film having a thickness of 250 nm was formed on the substrate. As the result of analyzing the crystal structure of the thin film by XRD, the thin film was $SrBi_2Ta_2O_9$ of a perovskite structure.

EXAMPLE 5

Production of thin film of tungsten bronze type $(Sr_{0.75}Ba_{0.25})Nb_2O_6$ by CVD method:

In a raw material container capable of making bubbling supply were charged 26.2 g (0.030 mole) of $Sr[Nb(OC_2H_5)_5(OC_2H_4OCH_3)]_2$ obtained in Example 2 and 9.2 g (0.010 mole) of $Ba[Nb(OC_2H_5)_5(OC_2H_4OCH_3)]_2$ followed by mixing well and the mixture was maintained at 180° C. The raw material container was connected to a vacuum thermal CVD apparatus system (total pressure 5 Torr), 50 sccm of an argon gas was introduced thereinto by bubbling and sent to a thermal decomposition chamber together with the vapors of $Sr[Nb(OC_2H_5)_5(OC_2H_4OCH_3)]_2$ and $Ba[Nb(OC_2H_5)_5(OC_2H_4OCH_3)]_2$ evaporated. The gas containing the vapors was mixed with 20 sccm of an oxygen gas at the inlet of the thermal decomposition chamber. In the thermal decomposition chamber, a $Pt/SiO_2/Si$ substrate was heated to 400° C., the above-described gas containing the vapors was introduced onto the substrate to cause a thermal decomposition accumulation for 30 minutes. Then, the amount of an oxygen gas introduced was increased, the temperature was raised, and a heat treatment was applied at 700° C. for 30 minutes. Thus, a thin film having a thickness of 250 nm was formed on the substrate. As the result of analyzing the crystal structure of the thin film by XRD, the thin film was a tetragonal tungsten bronze structure. A part of the thin film was decomposed in a wet method and as the result of applying an elemental analysis by an ICP-AES analysis, the composition of the thin film was $(Sr_{0.75}Ba_{0.25})Nb_2O_6$.

As described above, because the double alkoxide of niobium or tantalum and an alkaline earth metal of this invention shown by the formula I is a liquid at room temperature, is hard to be thermally dissociated, and has a vapor pressure of about 0.2 Torr at 190° C., a complex metal oxide dielectric thin film can be easily produced using the double oxide as the raw material. In particular, when the double oxide is used as a raw material for CVD, a film having the composition of the stoichiometric ratio can be easily formed, which becomes a great advantage in the production of semiconductor devices.

What is claimed is:

1. A compound represented by the following formula I:

$$M[N(OC_2H_5)_5(OC_2H_4OR)]_2 \qquad \text{I}$$

wherein M represents Sr or Ba, N represents Nb or Ta, and R represents an alkyl group having from 1 to 4 carbon atoms.

2. The compound according to claim 1, wherein R is $CH_3$.

3. A method of producing the compound as claimed in claim 1, which comprises reacting $N(OC_2H_5)_5$ and $M(OC_2H_4OR)_2$.

4. A method of producing the compound as claimed in claim 2, which comprises reacting $N(OC_2H_5)_5$ and $M(OC_2H_4OCH_3)_2$.

5. A method of producing the compound as claimed in claim 1, which comprises reacting $N(OC_2H_5)_5$ and $M(OC_2H_4OR)_2$ and then recovering the product by distillation.

6. A method of producing the compound as claimed in claim 2, which comprises reacting $N(OC_2H_5)_5$ and $M(OC_2H_4OCH_3)_2$ and then recovering the product by distillation.

7. A method of producing a dielectric thin film comprising $(Sr_pBa_q)Nb_2O_6$, wherein p+q=1, by chemical vapor deposition, which comprises the steps of:

decomposing or oxidizing compounds comprising $Sr[Nb(OC_2H_5)_5(OC_2H_4OR)]_2$, and $Ba[Nb(OC_2H_5)_5(OC_2H_4OR)]_2$, wherein R represents an alkyl group having from 1 to 4 carbon atoms; and exposing the decomposing or oxidizing compounds to a substrate, whereby the thin film is formed.

8. A method of producing a dielectric thin film comprising $(Sr_pBa_q)Nb_2O_6$, wherein p+q=1, by chemical vapor deposition, which comprises the steps of:

decomposing or oxidizing compounds comprising $Sr[Nb(OC_2H_5)_5(OC_2H_4OCH_3)]_2$, and $Ba[Nb(OC_2H_5)_5(OC_2H_4OCH_3)]_2$; and exposing the decomposing or oxidizing compounds to a substrate, whereby the thin film is formed.

9. A method of producing a bismuth layered ferroelectric thin film comprising $SrBi_2(Ta_xNb_y)_2O_9$, wherein x+y=1, by chemical vapor deposition, which comprises the steps of:

decomposing or oxidizing compounds comprising $Sr[Ta(OC_2H_5)_5(OC_2H_4OR)]_2$ and $Sr[Nb(OC_2H_5)_5(OC_2H_4OR)]_2$, wherein R represents an alkyl group having 1 to 4 carbon atoms; and exposing the decomposing or oxidizing compounds to a substrate, whereby the thin film is formed.

10. A method of producing a bismuth layered ferroelectric thin film comprising $SrBi_2(Ta_xNb_y)_2O_9$, wherein x+y=1, by chemical vapor deposition, which comprises the steps of:

decomposing or oxidizing compounds comprising $Sr[Ta(OC_2H_5)_5(OC_2H_4OCH_3)]_2$, and $Sr[Nb(OC_2H_5)_5(OC_2H_4OCH_3)]_2$; and exposing the decomposing or oxidizing compounds to a substrate, whereby the thin film is formed.

11. A method of producing a thin film comprising the steps of:

decomposing or oxidizing a compound comprising $M[N(OC_2H_5)_5(OC_2H_4OR)]_2$, wherein M represents Sr or Ba, N represents Nb or Ta, and R represents an alkyl group having from 1 to 4 carbon atoms; and exposing the decomposed or oxidized compound to a substrate, whereby the thin film is formed.

12. A method of producing a thin film, as in claim 11 wherein:

R comprises $CH_3$.

13. A method of producing a thin film, as in claim 11 wherein:

the step of decomposing or oxidizing comprises chemical vapor deposition.

14. A method of producing a thin film, as in claim 11 wherein:

the step of decomposing or oxidizing comprises chemical vapor deposition.

* * * * *